United States Patent [19]
Zito

[11] Patent Number: 5,617,727
[45] Date of Patent: Apr. 8, 1997

[54] CONTROLLED MULTIPLE STORAGE VESSEL GAS TRAP

[75] Inventor: Richard R. Zito, Tucson, Ariz.

[73] Assignee: Richard R. Zito R & D Corp., Tucson, Ariz.

[21] Appl. No.: 653,498

[22] Filed: May 24, 1996

[51] Int. Cl.$^6$ .................................................. B01D 8/00
[52] U.S. Cl. .................................................. 62/55.5; 55/269
[58] Field of Search .............................. 62/55.5; 55/269

[56] References Cited

U.S. PATENT DOCUMENTS

| | | | |
|---|---|---|---|
| 3,677,279 | 7/1972 | Lenfant | 137/197 |
| 3,712,074 | 1/1973 | Boissin | 62/55.5 |
| 3,731,466 | 5/1973 | Kunsman et al. | 55/386 |
| 3,859,807 | 1/1975 | Benedict et al. | 62/55.5 |
| 3,859,808 | 1/1975 | Benedict | 62/55.5 |
| 4,361,418 | 11/1982 | Tscheppe | 62/55.5 |
| 4,363,639 | 12/1982 | Gladon | 55/95 |
| 4,535,597 | 8/1985 | Missimer et al. | 62/55.5 |
| 4,597,267 | 7/1986 | Forrest | 62/55.5 |
| 4,615,387 | 10/1986 | Johnson et al. | 166/242 |
| 5,161,382 | 11/1992 | Missimer | 62/55.5 |
| 5,199,509 | 4/1993 | Wright et al. | 175/50 |
| 5,228,514 | 7/1993 | Worden et al. | 165/155 |
| 5,261,250 | 11/1993 | Missimer | 62/55.5 |
| 5,265,431 | 11/1993 | Gaudet et al. | 62/55.5 |
| 5,303,558 | 4/1994 | Caton et al. | 62/55.5 |
| 5,408,868 | 4/1995 | Ortega et al. | 73/61.41 |

FOREIGN PATENT DOCUMENTS

| 739453 | 9/1969 | Belgium | F16R 45/02 |
|---|---|---|---|
| 7013893 | 4/1970 | France | B01D 5/00 |

*Primary Examiner*—Ronald C. Capossela

[57] ABSTRACT

A gas trap having several independently controlled storage vessels (140,150). Access to each vessel is achieved via pneumatic valves (80,90), and these pneumatic valves are, in turn, controlled by solenoid valves (300, 380). The solenoid valves receive their electrical power from a relay system (520) which is controlled by a computer (550).

6 Claims, 1 Drawing Sheet

5,617,727

CONTROLLED MULTIPLE STORAGE VESSEL GAS TRAP

BACKGROUND

1. Field of Invention

This invention describes a computer controlled device, having several independently controlled storage vessels, for trapping various types of gases.

2. Description of Prior Art

There is a need for a computer controlled device which can collect multiple gas samples in sequence. There are many types of gas traps in the prior art, but none have these characteristics. Most prior art gas traps are intended for very specific tasks such as gas chromatography (Kunsman et al.; U.S. Pat. No. 3,731,466; 1973), crude oil detection (Ortega et al.; U.S. Pat. No. 5,408,868; 1995), distribution of corrosion inhibitors in gas (Johnson et al.; U.S. Pat. No. 4,615,387; 1986), or trapping gases released specifically from mud (Wright et al., U.S. Pat. No. 5,199,509; 1993). Finally, the inventions of Benedict (U.S. Pat. No. 3,859,808; 1975) and Benedict et al (U.S. Pat. No. 5,859,807; 1975) describe a trap used in the processing of uranium hexafluoride. These devices have very specific structural features, different from those of the current invention, which make them unsuitable for general laboratory gas collection and analysis.

Another class of traps is intended to capture certain gases for later disposal. Storage of samples is not the aim of these inventions. For example, the "automatic gas trap" of Lenfant (U.S. Pat. No. 3,677,279; 1972) collects undesirable gas accumulations in liquid filled chambers. The patent by Gladon (U.S. Pat. No. 4,365,659; 1982) describes a trap intended to remove atmospheric pollutants by bubbling air through a chemically active solution, and the patent by Caton et al. (U.S. Pat. No. 5,503,558; 1994) describes an invention relating to traps and filters for removing gaseous materials from exhaust gases of semiconductor manufacturing equipment. Finally, the patent by Boissin (U.S. Pat. No. 3,712,074; 1973) describes a cryogenic trap for removal of gases from a chamber. None of these inventions is a gas sampling apparatus capable of storing a series of independent, individual, samples.

Some industrial gas traps seek reuse of recovered gases. For example, the gas trap by Missimer (U.S. Pat. No. 5,261,250; 1993) describes a two stage apparatus capable of recapturing vapors lost during various industrial processes. Here, there is no interest in storing numerous samples, or in computer control, only bulk recovery of volatile substances. The invention by Worden et al. (U.S. Pat. No. 5,228,514; 1993) describes a gas trap which captures volatile gases by cooling and then releases them later by heating for later analysis. However, the Worden apparatus, which has a very different structure than the present apparatus, has no capacity for, storing multiple samples or computer control.

SUMMARY OF THE INVENTION

Accordingly, several objects and advantages of the present invention are:
(a) to provide a trap capable of storing several samples of gas;
(b) to provide a gas trap capable of computer control;
(c) to provide a gas trap which will seal itself and preserve valuable samples in the event of a power failure;
(d) to provide a gas trap made of ultra-clean, non-contaminating, valves and parts;
(e) to provide a gas trap that requires little or no maintenance, except for occasional replacement of absorbent materials.

Further objects and advantages of the present invention will become apparent from a consideration of the ensuing description and drawings.

Figure 1:
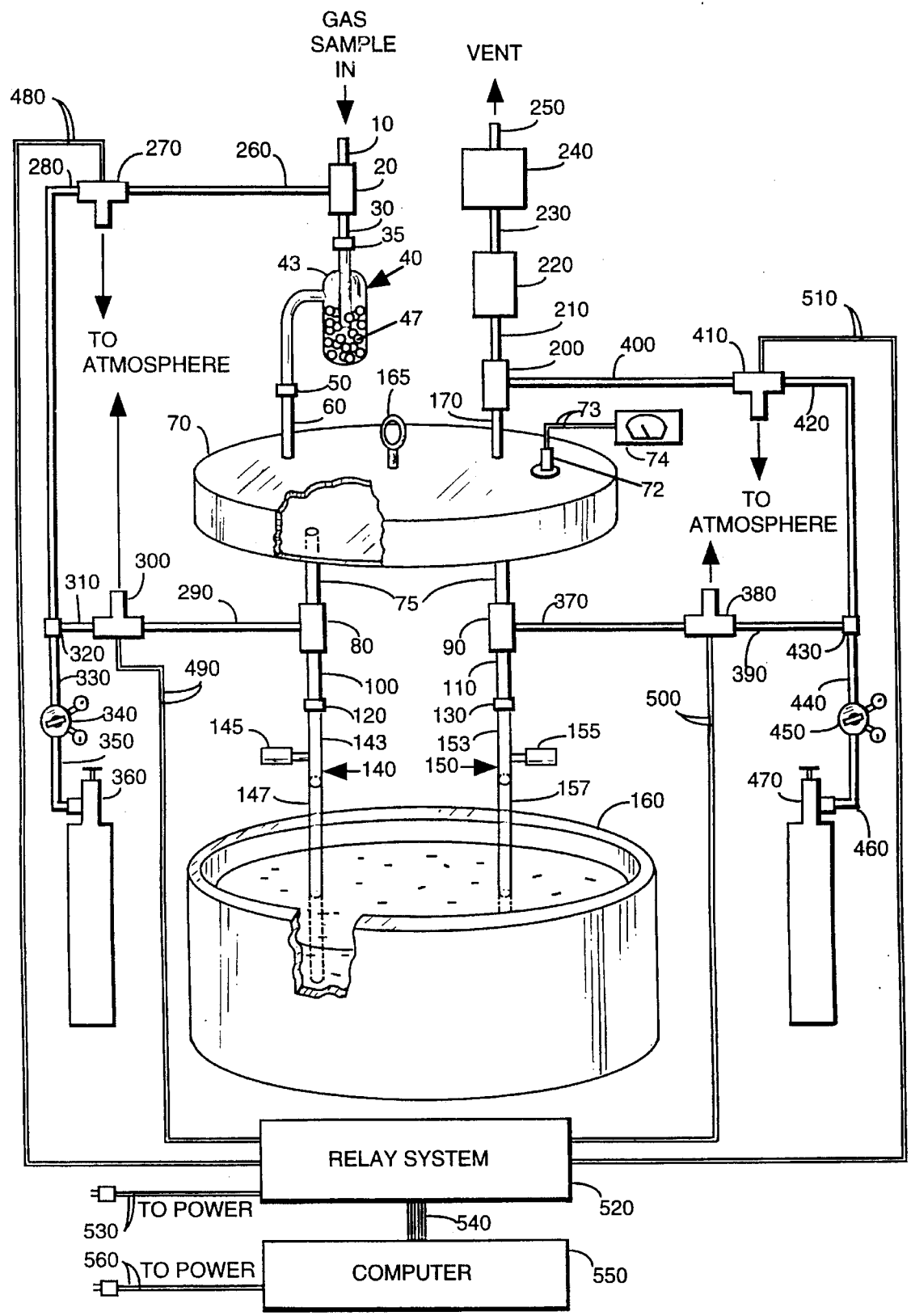
FIG. 1 shows a system overview with cutaways.

Reference Numerals in Drawings:
10 inlet tube
20 initial pneumatic valve
30 initial valve outlet tube
35 inlet union
40 foretrap
43 vacuum trap
47 absorbent
50 foretrap outlet union
60 tube
70 canister
72 pressure sensor head
73 sensor wires
74 display unit
75 canister outlet tubes
80 left secondary pneumatic valve
90 right secondary pneumatic valve
100 left secondary valve outlet tube
110 right secondary valve outlet tube
120 left outlet tube union
130 right outlet tube union
140 left valved storage vessel
143 left valve body
145 left valve body handle
147 left storage vessel bottom
150 right valved storage vessel
153 right valve body
155 right valve body handle
157 right storage vessel bottom
160 refrigerant filled Dewar
165 support loop
170 canister evacuation tube
200 pneumatic evacuation valve
210 evacuation valve outlet tube
220 high vacuum pump
230 high vacuum pump outlet tube
240 roughing pump
250 roughing pump outlet tube
260 initial pneumatic valve control pressure line
270 initial solenoid valve
280 initial solenoid valve inlet tube
290 left secondary pneumatic valve control pressure line
300 left secondary solenoid valve
310 left secondary solenoid valve inlet tube
320 left three-way union left
330 intermediate pressure line
340 left regulator
350 left high pressure line
360 left gas tank
370 right secondary pneumatic valve control pressure line
380 right secondary solenoid valve
390 right secondary solenoid valve inlet tube
400 pneumatic evacuation valve control pressure line
410 evacuation solenoid valve
420 evacuation solenoid valve inlet tube 430 right three-way union
440 right intermediate pressure line
450 right regulator
460 right high pressure line
470 right gas tank
480 pair of initial solenoid valve electrical power supply lines
490 pair of left secondary solenoid valve electrical power lines
500 pair of right secondary solenoid valve electrical power lines
510 pair of evacuation solenoid valve electrical power lines
520 relay system
530 pair of relay system power line
540 relay control signal lines
550 computer
560 pair of computer power lines

DETAILED DESCRIPTION OF INVENTION

Referring to FIG. 1, a gas sample enters the apparatus through an inlet tube 10. Inlet tube 10 is connected to an initial pneumatic valve 20. When pneumatic valve 20 is open, the gas sample can pass through the pneumatic valve into an initial valve outlet tube 30. Tube 30 is connected by an inlet union 55 to a foretrap 40. The gas sample passes through union 35 and goes into foretrap 40 for removal of unwanted impurities.

Foretrap 40 is composed of a standard vacuum trap 43 filled with an absorbent 47. Absorbent 47 may be any one of several chemical compounds. Calcium chloride ($CaCl_2$) can be used to absorb water, lead nitrate [$Pb(NO_3)_2$] absorbs $H_2S$, copper (Cu) and silver (Ag) metal absorbs $SO_2$, Ascarite-brand carbon dioxide absorbent (Ascarite is a trademark of LECO Corporation, St. Joseph, Mich.) absorbs $CO_2$, molecular sieve absorbs all gases except H and He, and silica gel can be used to absorb CO. Other absorbents are also possible for absorbing any of the compounds just described or other compounds. Furthermore, other absorbents may be used in combination with the absorbents above.

After the gas sample has been cleaned in foretrap 40, it passes through a foretrap outlet union 50 which joins foretrap 40 to a tube 80. If unions 35 and 50 are loosened, foretrap 40 may be removed for replacement of absorbent 47 when that service is required. Tube 60 is welded to the top of a canister 70. Other methods of joining tube 60 to canister 70 are also possible. Tube 60 conducts the gas sample into canister 70. The gas sample pressure can be monitored by a pressure sensor head 72 which is electrically connected by a pair of sensor wires 73 to a display unit 74. Sensor head 72 is usually a Penning gauge head, although other types of pressure gauge heads are possible. It is also possible to place the pressure sensor head in a different location on the system, or even, although inconvenient, to leave it out completely.

There are several ways to build canister 70. A short piece of pipe can have top and bottom plates welded to it, as shown in FIG. 1, to form a hollow central region. Another possibility is to take two vacuum system blanks, place a copper vacuum seal between them and bolt the two blanks together. If the central region of one or both of the facing surfaces of the blanks is milled down, a hollow interior region is created. Still another way of building the canister 70 is to form a hollow torus out of pipe, tubing, or vacuum fittings such as elbows, short nipples, and "T-sections". Other construction techniques may be possible.

The gas sample in canister 70 can now spread into canister outlet tubes 75 which are welded onto canister 70. Other methods of attachment may be possible. The lower ends of tubes 75 are attached to left and right secondary pneumatic valves 80 and 90, respectively. The attachment of tubes 75 to valves 80 and 90 can be accomplished by pipe thread, or by means of a crushable ferrule, but it is much more usual to use a face seal. Of course, it is also possible to have more than just two secondary pneumatic valves hanging from the canister. Now, if pneumatic valve 80 is open and pneumatic valve 90 is closed, then the gas sample will pass through pneumatic valve 80 into a left secondary valve outlet tube 100, which is attached to pneumatic valve 80 by a face seal or another type of seal. The lower end of tube 100 is connected to a left outlet tube union 120 which employs O-rings, or other devices, to make a vacuum tight seal to tube 100. The lower end of union 120 also employs an O-ring seal for vacuum tight attachment to the top of a left valved storage vessel 140. Union 120 is a standard commercial item, one supplier being the Cajon Company, Macedonia, Ohio. The union is sold under the unregistered name of "ultra-tort union". The vacuum tight union 120 allows a gas sample to pass from tube 100 into storage vessel 140. Naturally, if pneumatic valve 80 is closed and pneumatic valve 90 is open, a gas sample will pass through pneumatic valve 90, a right secondary valve outlet tube 110, a right outlet tube union 150, and into a right valved storage vessel 150.

Typically, storage vessels 140 and 150 are made of borosilicate glass, although other types of glass or metal storage vessels are possible. The manufacture of glass storage vessels involves starting with a commercially available valve body (denoted by left and right valve bodies 145 and 155, respectively, in FIG. 1). Valve bodies 145 and 155 have attached to them left and right valve body handles 145 and 155, respectively. The valve bodies are then straight sealed to the open end of left and right storage vessel bottoms 147 and 157, respectively. The bottoms 147 and 157 are formed by closing one end of a piece of borosilicate tubing with a torch.

Storage vessels 140 and 150 dip into a refrigerant filled Dewar 160. The depth to which the storage vessels 140 and 150 penetrate below the surface of the refrigerant is governed by raising or lowering the apparatus by a support loop 165. If the apparatus will be unattended for a long period of time, it will be necessary to insert the storage vessels 140 and 150 fairly deeply into the refrigerant. In fact, it may even be necessary to make storage vessels 140 and 150 with extra long bottoms 147 and 157 to provide extra penetration into the refrigerant. The refrigerant used in Dewar 160 may be isopropanol and dry ice, liquid nitrogen, a mixture of liquid and solid pentane, liquid neon, or other substances. The presence of the refrigerant eventually causes all, or some component, of the gas sample which was introduced into the apparatus to freeze in bottoms 147 and 157. Once the gas sample is frozen in place, storage vessels 140 and 150 may be manually closed by handles 145 and 155. Storage vessels 140 and 150 may now be removed from the apparatus, provided that both valves 80 and 90 are closed, by loosening the lower O-ring seal on unions 120 and 130. Once separated from the apparatus, the gases trapped in storage vessels 140 and 150 may be studied in a mass spectrometer, or other instruments, or used for other purposes.

Between introduction of gas samples it is necessary to evacuate all parts of the apparatus described up to this point. This is accomplished by pumping out any unwanted residual gases through a canister evacuation tube 170, which is connected to a pneumatic evacuation valve 200. When pneumatic valve 200 is open, unwanted gas expands through pneumatic valve 200, and an evacuation valve outlet tube 210, to be removed by a high vacuum pump 220. Pump 220 is an oil diffusion pump, turbomolecular pump, or another type of high vacuum pump. Pump 220 has a high vacuum pump outlet tube 230 which is connected to a roughing pump 240. Roughing pump 240 is usually, but not necessarily, a mechanical type of pump. Unwanted gases passing through pump. 220, tube 250, and roughing pump 240 are finally expelled through a roughing pump outlet tube 250.

The pneumatic valves 20, 80, 90, and 200 are standard gas controlled valves. Typically air, nitrogen, or some other gas at a pressure of about 80 psi (other pressures are also possible) is used to open and close the pneumatic valves. This control gas is isolated from the sample gas and does not mix with, or contaminate, the sample gas in any way. The control gas is conducted to pneumatic valve 20 through an initial pneumatic control pressure line 260, which is usually made of copper, although lines made of stainless steel, plastic, and other materials are possible. This patent application uses a pneumatic valve 20 that is normally closed when the gauge pressure in line 260 is zero. This type of valve will prevent the escape of gases already in the apparatus, or the introduction of new gases into the apparatus, in the event of a power failure. However, it is possible, although not as advantageous, to use normally open valves as well. The pressure in line 260 is controlled by an initial solenoid valve 270. Solenoid valve 270 is an electrically controlled three-way valve, and in the event of a power failure (zero voltage applied), vents to air so that zero gauge pressure remains in line 260. When a voltage is applied to solenoid valve 270, solenoid valve 270 connects line 260 to the gas pressure in an initial solenoid valve inlet tube 280. It should be noted that it may be possible to use other types of valves in place of the solenoid valve used in this preferred embodiment, so that the valve described above should not be considered a limitation on this application. The pneumatic valve 80 operates the same way as pneumatic valve 20, except that it is controlled by pressure in a left secondary pneumatic valve control pressure line 290. The pressure in line 290 is, in turn, controlled by a left secondary solenoid valve 300, which vents to air for zero applied voltage, and is fed by gas in a left secondary solenoid valve inlet tube 510. Tube 280 and tube 310 are both joined by a left three-way union 320 which is pressurized by a left intermediate pressure line 550 from the low pressure side of a left regulator 340. Regulator 340 is fed by gas from a left high pressure line 350 which is directly connected to a left gas tank 360. The control of pneumatic valves on the right side of the apparatus is similar to that on the left side. Pneumatic valve 90 is opened by gas pressure in a right secondary pneumatic valve control pressure line 570, which is, in turn, controlled by a right secondary solenoid valve 580. Solenoid valve 380 vents to air for zero applied voltage, and is fed pressurized gas by a right secondary solenoid valve inlet tube 590. Similarly, pneumatic valve 200 is controlled by the gas pressure in a pneumatic evacuation valve control pressure line 400, which is, in turn, controlled by an evacuation solenoid valve 410. Again, solenoid valve 410 vents to air when zero voltage is applied to it. This venting produces zero gauge pressure in line 400, which causes pneumatic valve 200 to close, thereby preventing accidental loss of a gas sample in the event of a power failure. Solenoid valve 410 is fed by an evacuation solenoid valve inlet tube 420. Tube 420 joins tube 390 at a right three-way union 430 which is fed gas from a right intermediate pressure line 440 that leads to a right regulator 450. Regulator 450 is connected to a right high pressure line 460, and line 460 is connected to a right gas tank 470. It should be noted that the left and right side of the apparatus can share a common intermediate pressure line, regulator, high pressure line, and gas tank. In this latter design variation, three-way unions would be replaced by a multi-port manifold and all the solenoid valve inlet tubes would feed into this manifold which would be pressurized by the single intermediate pressure line from a single regulator, high pressure lines and tank. Next, the electrical control of the solenoid valves will be discussed.

Solenoid valves 270, 500, 380, and 410 are all electrically controlled three-way solenoid valves which pressurize lines 260, 290, 570, and 400 respectively when they receive a voltage, as previously discussed. Solenoid valve 270 receives its voltage through a pair of initial solenoid valve electrical power lines 480, solenoid valve 300 receives voltage from a pair of left secondary solenoid valve electrical power lines 490, solenoid valve 580 receives voltage from a pair of right secondary solenoid valve electrical power lines 500, and finally, solenoid valve 410 receives its voltage from a pair of evacuation solenoid valve electrical power lines 510. Power lines 480, 490, 500, and 510 are all connected to the output terminals of a relay system 520. Relay system 520 is a commercially available module which is manufactured and sold by Omega Engineering, Inc., Stamford, Conn. Relay systems from other companies may also be used, or custom made relay systems can be constructed from individual relays if desired. By turning different relays on or off electrical power can be sent to, or cut off from, various solenoid valves, thereby turning them on or off. The power used to perform this operation comes from a pair of relay system power lines 530. The signal used to turn different relays on or off in relay system 520 comes from relay control signal lines 540, which are, in turn, connected to a computer 550 powered by a pair of computer power lines 560. The computer 550 can, of course, also be powered by batteries.

Operation—FIG. 1

Operation begins with initialization of the system. First fill Dewar 160 with refrigerant if required. Then, turn on roughing pump 240. Valve bodies 143 and 153 should be in the open position. The interior of the system can now be evacuated so that a pressure of about 1 Torr (although other pressures are possible) exists in all parts through which a gas sample will pass. This pressure may be monitored on display 74. Next, turn on high vacuum pump 220 and wait until the pressure drops to about $10^{-5}$ Torr (although other pressures are possible). The parts to be evacuated include all parts between pneumatic valves 20 and 200 down to, and including, storage vessels 140 and 150. This initial configuration is achieved when computer 550 sends a signal to relay system 520 and closes the electrical relay contacts which provide a voltage to solenoid valves 500, 580, and 410 (but not solenoid valve 270). This action allows control gas pressure to open pneumatic valves 80, 90, and 200, so that the interior of the system can be evacuated. Once evacuation is accomplished as indicated by pressure gauge display 74, pneumatic valve 200 can be closed by removing the voltage to solenoid valve 410 and venting line 400 to air. The system is now configured to receive gas samples.

Suppose it is desired to fill left valved storage vessel 140 first. The required procedure involves closing pneumatic valve 90 by removing the voltage from solenoid valve 380. Closing pneumatic valve 90 will prevent the gas sample from entering right valved storage vessel 150. Now, pneumatic valve 20 can be opened by applying a voltage to solenoid valve 270. This procedure will allow the gas sample to enter the interior of the system, including storage vessel 140. Once the gas sample fills the system, pneumatic valve 20 can be closed by removing the voltage from solenoid valve 270. If the gas sample is in a form ready for collection, and if the pressure of the gas sample is high enough to allow a sufficient amount of gas to fill storage vessel 140 for the intended purpose, then pneumatic valve 80 can be closed by removing the voltage from solenoid 500. The gas sample is now safely stored. Any extra gas remaining in the system can now be removed by applying a voltage to solenoid valve 410. Solenoid valve 410 will then open pneumatic valve 200, thereby evacuating the system volume above the storage vessels. However, it is often the case that the gas sample filling the interior of the system is so precious that all of the gas sample must be condensed into storage vessel 140 for analysis. Or, the gas sample filling the system may be a mixture of gases, only one component of which a researcher is interested in. In order to collect all of the gas sample in the system, or a component of interest, freezing methods can be used. For example, suppose a researcher desires to collect a minute quantity of carbon dioxide to be used for carbon dating, or separate carbon dioxide from a mixture of carbon dioxide, oxygen, nitrogen, and argon (i.e. separate carbon dioxide from air). The procedure of choice is now to leave pneumatic valve 80 open while the left storage vessel bottom 147 is dipped into refrigerant filled Dewar 160. If liquid nitrogen is used as the refrigerant, then carbon dioxide will quickly form in bottom 147 as a layer of dry ice, but volatile substances like oxygen, nitrogen and argon will not condense if the sample pressure is much less than about one third of an atmosphere. During carbon dioxide condensation the pressure indicated on display 74 will drop. Once the pressure stops dropping and levels off, condensation of carbon dioxide is complete. Pneumatic valve 200 may now be opened by applying a voltage signal to solenoid 410. When this action is taken, the volatile gases oxygen, nitrogen, and argon will be pumped away (as indicated by the reading on display 74) leaving pure frozen carbon dioxide in storage vessel 140. Pneumatic valves 80 and 200 may now be closed by removing the voltage from solenoid valves 500 and 410 respectively. The example just given involving the trapping of carbon dioxide is only meant to be illustrative and should not be considered a limitation on this patent application. The system is now ready to receive its second gas sample.

With pneumatic valve 80 closed, pneumatic valve 90 is opened by applying a voltage to solenoid valve 380. The next gas sample Tan now be allowed to enter the system by opening pneumatic valve 20. After gas sample introduction is complete, pneumatic valve 20 can be closed. If it is desired to only trap some gas in storage vessel 150, then pneumatic valve 90 can be closed as well. However, if freezing the gas sample into bottom 157 is required, then it is necessary to wait a predetermined time before closing pneumatic valve 90. Or, the decision as to when to close valve 90 can be made by feeding the pressure from display 74 to the analogue to digital conversion board of computer 550 via a jack that is often provided on the back of commercially available pressure displays. When the pressure drops to some predetermined level computer 550 makes the decision to open the appropriate relay in relay system 520, thereby removing the voltage to solenoid valve 380 and closing pneumatic valve 90. Unwanted residual gas above storage vessel 150 can now be pumped away by opening pneumatic valve 200 until display 74 indicates that a suitable vacuum exists within the apparatus. Pneumatic valve 200 can now be closed. If the system has more than two storage vessels, the procedure described in this paragraph can be repeated in a similar way until all storage vessels are filled. Naturally, the storage vessels can be filled in any order desired. Next, removal of filled storage vessels will be discussed.

Once storage vessels 140 and 150 are filled, valve bodies 145 and 155 should be closed manually by turning handles 145 and 155. Next, the apparatus might have to be raised by support loop 165 to pull the left and right storage vessel bottoms out of the refrigerant filled Dewar 160. The same thing can be accomplished by lowering Dewar 160. Now, the lower end of unions 120 and 150 can be loosened and storage vessels 140 and 150 pulled down and removed from the unions. This procedure is safe since pneumatic valves 80, 90, and 200 are all closed, thereby preventing air from entering the system and burning the pump oil in high vacuum pump 220. The storage vessels can now be attached to a mass spectrometer, or any other instrument for analysis of storage vessel contents. Finally, the system shutdown procedure will be discussed.

After gas sample filled storage vessels are removed, empty (except for air) storage vessels should be attached. The valve bodies of these storage vessels should be in the open position. Next, pneumatic valves 80, 90, and 200 should be opened so that high vacuum pump 220 and roughing pump 240 can remove the small amount of air that was originally trapped in the replacement storage vessels. Pneumatic valves 80, 90, and 200 can now be closed and the apparatus returned to its original position in Dewar 160 by means of support loop 165. Of course, during shutdown it doesn't mater if refrigerant evaporates from Dewar 160. Finally, high vacuum pump 220 should be shut off to prevent any pump oil from burning. However, roughing pump 240 should always be left on. The system pressure will be about i Tort between times when the apparatus is in use. Of course, long term storage will require both high vacuum pump 220 and roughing pump 240 to be turned off. During long term storage close both the inlet tube 10 and roughing pump outlet tube 250 with some type of air tight plug.

Summary, Ramifications, and Scope

Accordingly, the reader will see that the gas trap described in this patent application is capable of being computer controlled and can store several gas samples. Several minor variations on the gas trap described in this application are described below.

First, when absorbent 47 is replaced by glass beads, or other types of beads, having many possible shapes or sizes that fit into vacuum trap 43, and the outside wall of vacuum trap 43 is cooled with a refrigerant like isopropanol and dry ice, liquid nitrogen, liquid and solid pentane, or liquid neon, foretrap 40 becomes a cryogenic trap capable of capturing a variety of gases, and passing others, depending on the refrigerant chosen. Refrigerants other than those listed above may also be used. Furthermore, cooling may also be used in combination with chemical absorbents such as, but not limited to, those listed above in the section entitled "Detailed Description of Invention". Sometimes several identical foretrap 40 units must be connected together in series or parallel in order to completely remove certain impurities from the gas sample that one ultimately wishes to store. Or, several different types of foretrap 40 units must be connected together to remove several different types of undesirable species. In situations where a sufficiently complex combination of foretraps is involved it may even be necessary to supply the combination with its own system of vacuum pumps in order to properly evacuate the combination between introduction of different gas samples. Finally, it should be noted that in cases where the incoming gas sample is already clean there is no need for foretrap 40, and in that case the gas sample may be injected directly into tube 60 fop conveyance to canister 70.

Second, all parts of the apparatus are preferably made of stainless steel, except for the vacuum trap 45 and the left and right valved storage vessels 140 and 150, respectively, which are usually made of borosilicate glass. Such a system is very clean and does not adsorb species from one sample and later release them to contaminate another sample. However, it is entirely possible to use other metals, glasses and plastics for the construction of the apparatus. These building materials include, but are not limited toy copper, brassy aluminum, and carbon steel for the metal parts. Fused silica, Vycor-brand high silica glass (Vycor is a trademark of Corning Glass Works, Corning N.Y.), and soda lime glass may be used for the vacuum trap and the storage vessels, although other glasses and even metals and plastics are possible. Teflon-brand PTFE (Teflon is a Trademark of E.I. dupont de Numours & Co., Wilmington, Del.), neoprene, synthetic rubber, or fluorocarbon elastomer, may be used for the seals in the unions and valve bodies 143 and 153. Other elastomers may also be possible for seals, and other parts of the apparatus as well. A variety of plastics, metals and other substances may be used for handles such as 145 and 155.

Another variation on the basic theme of this invention involves the pneumatic valves. There are two basic types. There are directionless valves whose inlet and outlet ends are functionally identical so that they can be used in either of two orientations, and there are valves which only seal well when the flow is in one direction. Either type will work well in the invention described in this application. However, when valves with a direction are used care must be taken to insure that the direction of flow of pneumatic valve 20 points into the system since the pressure outside the system will generally be higher than the gas sample pressure inside the system. Pneumatic valves 80 and 90 should have a flow direction pointing toward the storage vessels if only frozen samples having a very low vapor pressure are stored. For gaseous samples it is often best to rotate the valves so that the flow direction points away from the storage vessel. Finally, the flow direction of pneumatic valve 200 should point toward the vacuum pumps.

The valve bodies 145 and 155 may also have a specified flow direction, or they may be directionless. For directional valves the flow direction should usually point away from the storage vessel bottoms 147 and 157.

In the case where the researchers intention is only to collect gaseous samples it is possible to omit Dewar 160.

In cases where manual control is desired, the pneumatic valves can have a manual override or by-pass.

The configuration of the vacuum pumps offers other possible variations in the design of the apparatus. For example, it is common in vacuum system design to use a high vacuum pump by pass so that roughing pump 240 can be applied directly to the system without having to work through high vacuum pump 220.

Standard commercial parts, such as the three-way union "T"), may be joined to other parts by any vacuum tight method, including pipe threads, crushable ferrules, face seals, weld seals, or other methods of connection.

Finally, support loop 165 may be replaced by other types of support devices. These devices can be attached to the top of canister 70 by welding, or, if the top of canister 70 is thick enough, screws may be used provided they do not cause an air leak by penetrating into canister 70.

It should be noted that although this application contains many specificities, these should not be construed as limiting the scope of this invention but merely providing illustrations of some of the presently preferred embodiments of this invention.

I claim:

1. A gas trap of the type comprising:

A) an initial pneumatic valve, whereby gas samples can be let into said gas trap, B) a foretrap connected to the outlet of said initial pneumatic valve, whereby said gas samplers may be cleaned, C) a canister connected to said foretrap, whereby said gas samples may be temporarily stored, D) a plurality of secondary pneumatic valves connected to said canister, whereby said gas samples may be allowed to leave said canister by any one of several routs, E) a plurality of valved storage vessels connected to said secondary pneumatic valves in a one-to-one fashion, whereby said gas samples may be stored for periods of time longer than those for said canister, F) a pneumatic evacuation valve connected to said canister, whereby said canister may be evacuated, G) a roughing pump connected to said pneumatic evacuation valve, whereby said canister may be evacuated, H) a high vacuum pump connected to said roughing pump, whereby said canister may be more thoroughly evacuated, I) an initial solenoid valve connected to said initial pneumatic valve, whereby said initial pneumatic valve may be controlled, J) a plurality of secondary solenoid valves connected to said secondary pneumatic valves in a one-to-one fashion, whereby said secondary pneumatic valves may be controlled, K) an evacuation solenoid valve connected to said pneumatic evacuation valve, whereby said pneumatic evacuation valve may be controlled, L) a plurality of pressure lines such that one of said pressure lines is connected to said initial solenoid valve, and another of said pressure lines is connected to said evacuation solenoid valve, and said pressure lines remaining are connected to said secondary solenoid valves in a one-to-one fashion, whereby pressurized control gas may be supplied to all solenoid valves, M) a means for connecting said pressure lines together so that they all have substantially the same internal control gas pressure, N) a regulator connected to said means, whereby control gas may be supplied to said means, and O) a gas tank connected to said regulator, whereby control gas may be supplied to said regulator.

2. The gas trap of claim i further including a refrigerant filled Dewar into which the bottoms of said valved storage vessels may be immersed.

3. A gas trap of the type comprising:

A) an inlet tube, whereby gas samples may enter said gas trap,

B) a canister connected to said inlet tube, whereby said gas samples may be temporarily stored, C) a plurality of secondary pneumatic valves connected to said canister, whereby said gas samples may be allowed to leave said canister by several routs, D) a plurality of valved storage vessels connected to said secondary pneumatic valves in a one-to-one fashion, whereby said gas samples may be stored for periods of time longer than those for said canister, E) a pneumatic evacuation valve connected to said canister, whereby said canister may be evacuated, F) a roughing pump connected to said pneumatic evacuation valve, whereby said canister may be evacuated, G) a high vacuum pump connected to said roughing pump, whereby said canister may be more thoroughly evacuated, H) a plurality of secondary solenoid valves connected to said secondary pneumatic valves in a one-to-one fashion, whereby said secondary pneumatic valves may be controlled, I) an evacuation solenoid valve connected to said pneumatic evacuation valve, whereby said pneumatic evacuation valve may be controlled, J) a plurality of pressure lines such that one of said pressure lines is connected to said evacuation solenoid valve, and said pressure lines remaining are connected to said secondary solenoid valves in a one-to-one fashion, whereby pressurized control gas may be supplied to all solenoid valves, K) a means for connecting said pressure lines together so that they all have substantially the same internal control gas pressure, L) a regulator connected to said means, whereby control gas may be supplied to said means, and M) a gas tank connected to said regulator, whereby control gas may be supplied to said regulator.

4. The gas trap of claim 3 further including a refrigerant filled Dewar into which the bottoms of said valved storage vessels may be immersed.

5. A gas trap of the type comprising:

A) an inlet tube, whereby gas samples may enter said gas trap,

B) a canister connected to said inlet tube, whereby said gas samples may be temporarily stored, C) a plurality of secondary pneumatic valves connected to said canister, whereby said gas samples may be allowed to leave said canister by several routs, D) a plurality of valved storage vessels connected to said secondary pneumatic valves in a one-to-one fashion, whereby said gas samples may be stored for periods of time longer than those for said canister, E) a pneumatic evacuation valve connected to said canister, whereby said canister may be evacuated, F) a vacuum pump connected to said pneumatic evacuation valve, whereby said canister may be evacuated, G) a plurality of secondary solenoid valves connected to said secondary pneumatic valves in a one-to-one fashion, whereby said secondary pneumatic valves may be controlled, H) an evacuation solenoid valve connected to said pneumatic evacuation valve, whereby, said pneumatic evacuation valve may be controlled, I) a plurality of pressure lines such that one of said pressure lines is connected to said evacuation solenoid valve, and said pressure lines remaining are connected to said secondary solenoid valves in a one-to-one fashion, whereby pressurized control gas may be supplied to all solenoid valves, J) a means for connecting said pressure lines together so that they all have substantially the same internal control gas pressure, K) a regulator connected to said means, whereby control gas may be supplied to said means, and L) a gas tank connected to said regulator, whereby control gas may be supplied to said regulator.

6. The gas trap of claim 5 further including a refrigerant filled Dewar into which the bottoms of said valved storage vessels may be immersed.

* * * * *